United States Patent [19]
Fasel et al.

[11] Patent Number: 5,965,143
[45] Date of Patent: *Oct. 12, 1999

[54] IMMUNITY TO TRYPANOSOMATIDS SPECIES

[76] Inventors: Nicolas Joseph Fasel, No. 30, Bois Murat CH-1066, Epalinges, Switzerland; Theresa Ann Glaser, No. 67, Rue Grande Bourgade, FR 30700, Uzés, France

[*] Notice: This patent issued on a continued prosecution application filed under 37 CFR 1.53(d), and is subject to the twenty year patent term provisions of 35 U.S.C. 154(a)(2).

[21] Appl. No.: 08/668,255

[22] Filed: Jun. 20, 1996

[30] Foreign Application Priority Data

Mar. 12, 1996 [EP] European Pat. Off. ............. 96200665

[51] Int. Cl.$^6$ ..................... A61K 39/008; A61K 48/00; C12Q 1/68; C07H 21/00
[52] U.S. Cl. ..................... 424/269.1; 435/6; 435/320.1; 435/252.33; 514/44; 536/23.4; 536/23.5
[58] Field of Search ................................ 435/172.1, 243, 435/320.1, 325, 6, 252.33; 536/23.1, 23.4, 23.5; 424/269.1; 514/44

[56] References Cited

FOREIGN PATENT DOCUMENTS 0 309 898  4/1989  European Pat. Off. .

*Primary Examiner*—James Ketter
*Assistant Examiner*—William Sandals
*Attorney, Agent, or Firm*—Cushman Darby & Cushma; IP Group of Pillsbury

[57] ABSTRACT

The present invention relates to trypanosomatid histones in substantially isolated form for use as a protective antigen against trypanosomatid infection. These histones may be either isolated from the corresponding parasite or be produced by means of recombinant DNA techniques. For the latter purpose the invention also provides genes encoding histones and derivatives of the genes like other nucleic acids and gene products like peptides and proteins. The invention further provides diagnostic tests, pharmaceutical compositions and vaccines comprising the usual excipients and/or adjuvants and at least one histone, a histone encoding gene or a derivative thereof.

14 Claims, 9 Drawing Sheets

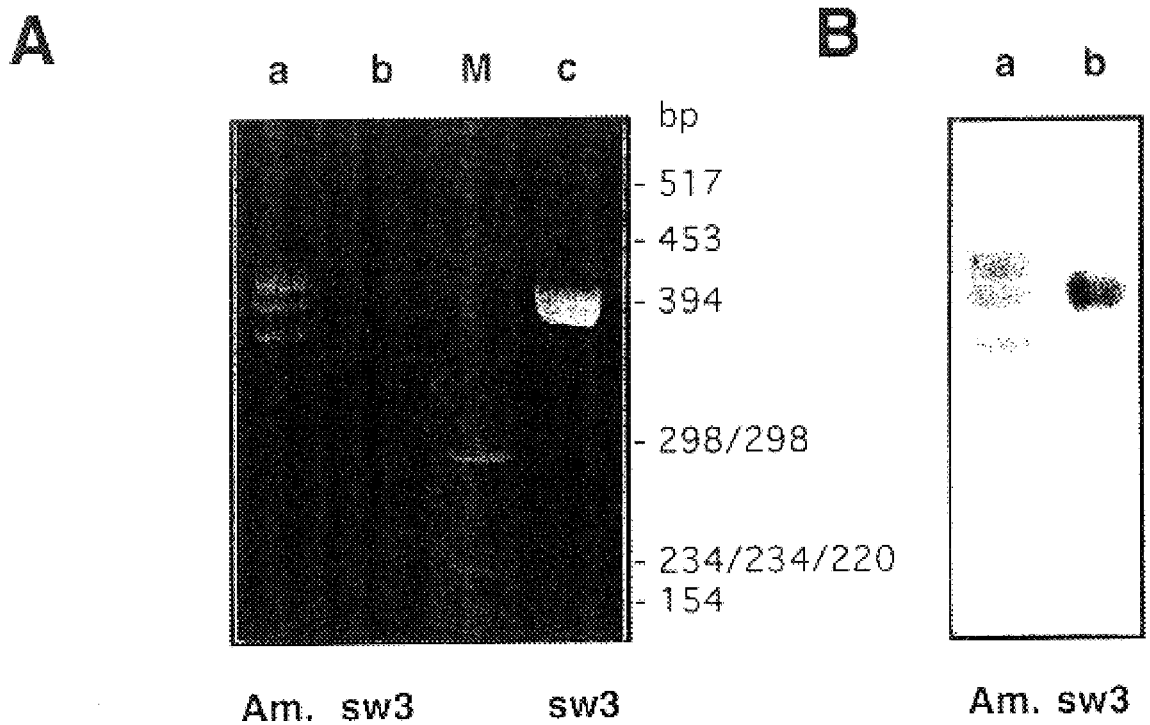
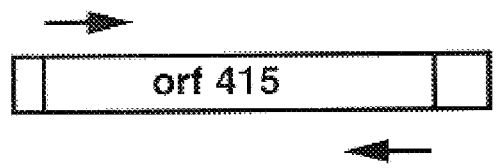
FIG. 5

```
       1
SW3  ATG TCC TCT AAT TCC GCC GCT GCT GCC GTT TCC GCC ACG ACC TCG CCG CAG AAG TCT    60
AA    M   S   S   N   S   A   A   A   A   V   S   A   T   T   S   P   Q   K   S

SW3  TCT CGC TCG TCG CCG AAG AGG GCG GCC GTG GGC AAG GCC GCG AAG AAG GTT GCC       120
AA    S   R   S   S   P   K   R   A   A   V   G   K   A   A   K   K   V   A

SW3  AAG AAG ACC GGC GCG AAG GTT GCG AAG AAG CCA GCG AAG ACC GGC AAG AAG CCA       180
AA    K   K   T   G   A   K   V   A   K   K   P   A   K   T   G   K   K   P

SW3  AAG AAG GTT GTG AAG AAG CCA GCG AAG AAG GTT GTG AAG AAG GCT GTG AAG GTG       240
AA    K   K   V   V   K   K   P   A   K   K   V   V   K   K   A   V   K   V

SW3  GCG AAG AAG GCT GTG AAG AAG GTT GTG AAG AAG ACC GCG AAG ACC GCG AAG AAA       300
AA    A   K   K   A   V   K   K   V   V   K   K   T   A   K   T   A   K   K

SW3  AAG AAG GCT GTG AAG AAG AAG AAG AAG GTT GTG AAG AAG TCG TCG AAG AAA           360
AA    K   K   A   V   K   K   K   K   K   V   V   K   K   S   S   K   K

SW3  TCC TCG GCG AAG AAG TAA GGT GCG CCA TCA TGC TTG CCC GTG GCT GAC TGT ACG CTC TTC
AA    S   S   A   K   K  STOP
```

FIG.6A

```
                                                                                           60
  1
A3  ATG TCC TCT AAT TCC GCC GCT GCC GTT TCC GCC ACG ACC TCG CCG CAG AAG TCT
AA   M   S   S   N   S   A   A   A   V   S   A   T   T   S   P   Q   K   S
                                                                                          120
A3  TCT CGC TCG TCG CCG AAG AGG GCG GCC GTG GCC AAG ACC GGC GCG AAG AAG GTT GCG
AA   S   R   S   S   P   K   R   A   A   V   A   K   T   G   A   K   K   V   A
                                                                                          180
A3  AAG AAG CCA GCG AAG GTT GCG GAG AAG AAG CCA GCG AAG GTT GTG AAG AAG CCA GCG
AA   K   K   P   A   K   V   A   E   K   K   P   A   K   V   V   K   K   P   A
                                                                                          240
A3  AAG AAG GTT GTG AAG AAG GCT GTG AAG AAG GCT GTG AAG AAG GTT GTG AAG AAG
AA   K   K   V   V   K   K   A   V   K   K   A   V   K   K   V   V   K   K
                                                                                          300
A3  AAG AAG GTT GTG AAG AAG TCG TCG AAT AAA TCC TCG GCG AAG TAA GGT GCG CCA
AA   K   K   V   V   K   K   S   S   N   K   S   S   A   K   *STOP  G   A   P

A3  GCT GTG AAG ACC GCG AAG
AA   A   V   K   T   A   K
```

```
                                                                                              60
P3  ATG TCC TCT AAT TCC GCC GCT GCC GTT TCC GCC ACG ACC TCG CCG CAG AAG TCT
AA   M   S   S   N   S   A   A   A   V   S   A   T   T   S   P   Q   K   S

120
P3  TCT CGC TCG TCG CCG AAG AGG GCG GCC GTG GCC GTG GGC AAG AAG ACC GGC GCC AAG AAG GTT GCC
AA   S   R   S   S   P   K   R   A   A   V   A   V   G   K   K   T   G   A   K   K   V   A

180
P3  AAG AAG CCA GCG AAG GCG GAG AAG GTT GCG AAG GTT GTG AAG AAG CCA GCG
AA   K   K   P   A   K   A   E   K   V   A   K   V   V   K   K   P   A

240
P3  AAG AAG GTT GTG AAG AAG GCT GTG AAG AAG GCT GTG AAG AAG GTT GTG AAG
AA   K   K   V   V   K   K   A   V   K   K   A   V   K   K   V   V   K

300
P3  GCT GTG AAG ACC GCG AAG AAG TCG TCG AAG AAA TCC TCG GCG AAG AAG TAA GGT GCG CCA
AA   A   V   K   T   A   K   K   S   S   K   K   S   S   A   K   K  STOP
```

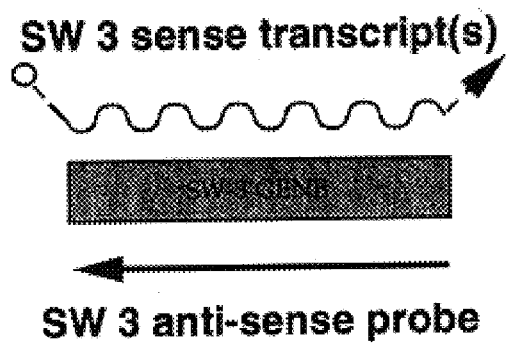
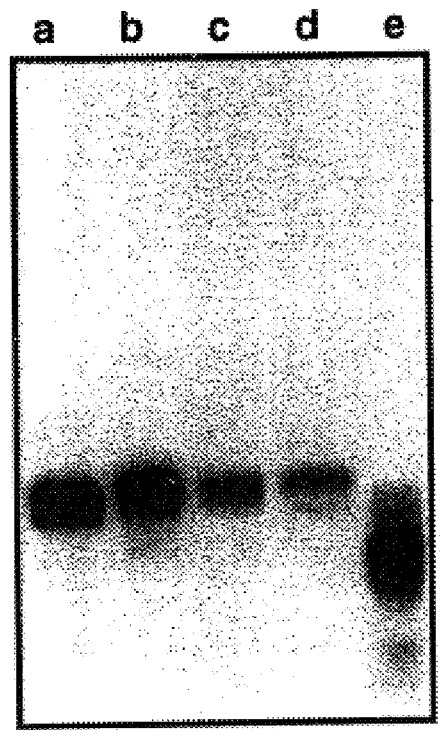
FIG. 7

IMMUNITY TO TRYPANOSOMATIDS SPECIES

BACKGROUND OF THE INVENTION

1. Field of the Invention

The present invention relates to genes and corresponding gene products (DNAs, RNAs and proteins) for use in vaccines and diagnostics specific for intracellular infectious agents, in particular for parasite infection, more in particular for trypanosomatids infection, in particular for Leishmania species infection, more in particular for cutaneous lesions inducing Leishmania, more in particular for *Leishmania major*.

2. Background Information

Leishmania, a member of the trypanosomatid family, is endemic in the tropical regions of America, Africa and the Indian subcontinent, in the sub-tropics of south-west Asia and in the Mediterranean. Infection with different species of the protozoan Leishmania, which is transmitted by sandflies, manifests itself as either self-healing cutaneous lesions, as neurological and cardiac disorders or as fatal visceral infections. The disease caused by Leishmania is generally called leishmaniasis.

Some forms of the disease are anthroponotic (transmitted only between humans), while others are zoonotic (involving a human reservoir). There are over 20 known species of Leishmania of which a dozen are associated with the various forms of leishmaniasis.

Based on the clinical pattern, the leishmaniasis can be classified into three groups. Cutaneous leishmaniasis is the most prevalent, producing skin ulcers which may take more than a year to heal. Mucocutaneous leishmaniasis initially causes similar lesions which may heal but reappear to cause hideous tissue destruction, primarily the nose and the mouth.

Finally, visceral leishmaniasis is a very severe systemic disease which is nearly always fatal if left untreated.

Since the mid-1980s a dramatic increase in the number of opportunistic Leishmania infections has been reported with the spread of the HIV epidemy to areas traditionally endemic for leishmaniasis. Currently the world wide prevalence of leishmaniasis is 12 million cases (see review Liew and O'Donnell, 1993) and 350 millions live in risk areas. The number of new cases of the disease each year being of the order of 1.5 million, of which 500.000 are visceral leishmaniasis.

Visceral leishmaniasis causes large scale epidemics and the number of cases varies greatly between the years. During 1991 there were large epidemics in India and Sudan. The number of cases in India alone may have been of the order of 250.000. It is estimated that visceral leishmaniasis may have killed 75.000 people in 1991.

The impact of cutaneous leishmaniasis is less dramatic, but it causes severe suffering in endemic areas, not least because of the social and psychological trauma associated with disfigurement. The importance attached to this by people in endemica areas is reflected in the old practice of leishmanization, which involves deliberate and risky infection with Leishmania in order to induce life-long immunity at the price of an ulcer and lesion on less exposed parts of the body.

During their life cycle, Leishmania grow in diverse environmental conditions, and differentiate through distinct developmental stages (see reviews Wilson 1990, Smith et al., 1994). In the sandfly vector, they grow as slender, flagellated infectious promastigotes. When the sandfly takes a blood meal, the parasites are transmitted to the human host where they are phagocytosed by resident skin macrophages. Within the macrophage lysosome, the parasites differentiate into round, non-flagellated amastigotes where they replicate until the macrophage is lysed. They are then released to infect other macrophages, or are taken up by a sandfly where they differentiate back to the promastigote stage to repeat their life cycle.

Life long protection achieved by natural or deliberate infection with Leishmania suggests that mass vaccination against this disease is feasible. Progress has been made in human clinical trials using whole killed parasites in vaccines against cutaneous leishmaniasis. However, problems have arisen such as the unavailability of reagents or variations in the host response to challenge infection. Furthermore, subcutaneous vaccination with heat-killed, avirulent or radio-attenuated promastigotes has often been ineffective or worse, exacerbated lesions. Thus, to avoid the risk of exacerbating naturally acquired infections by vaccination, it is essential to develop second generation vaccines, e.g. to use immunologically purified antigen(s) or derivative(s).

The clinical manifestations of human leishmaniasis can be mimicked in various inbred mouse strains following infection with *L.major.* The majority of strains (eg. CBA, C57BL/6) are relatively resistant to infection, developing only small lesions at the site of parasite inoculation, which are self-healing within a few weeks. In contrast, susceptible strains such as BALB/c mice develop severe-cutaneous lesions with no tendency to resolve and eventual fatal visceralization of the infection. In experimental murine leishmaniasis, it is generally accepted that $CD4^+$ T cells are responsible for resistance to infection with *L.major,* although $CD8^+$ lymphocytes have also been shown to play a role in the immunity against this parasite (Müller et al., 1989, Hill et al., 1989). Animal model studies have led to the delineation of two defined $CD4^+$ T lymphocyte subsets, Th1 and Th2, which may in part determine the outcome of *L.major* infection. Detailed discussions on the importance of the Th1/Th2 balance and the cytokine network(s) have been reported in recent reviews (Liew and O'Donnell, 1993; Milon et al., 1995). Briefly, the Th1 response is associated with the production of the cytokines IL-2 and γ-IFN, parasite killing, healing and protection, while the Th2 response is associated with the production of IL-4 and/or IL-10, disease progression and susceptibility (Heinzel et al., 1991; Scott, 1989). This pattern of lymphokine production has also been observed in human leishmaniasis (Reed and Scott, 1993). More recently, involvement of IL-12 in the immune response to Leishmania has been reported. IL-12 facilitates the development of a Th1 response by stimulating the production of γ-IFN and down-regulating that of IL-4 (Heinzel et al, 1993; Sypek et al; 1993).

Many studies using *Leishmania major* promastigotes derived antigens, such as the surface membranes gp63 and lipophosphoglycan (Russell et al, 1988), soluble extract (Scott et al, 1987) or gp63 epitopes (Yang et al, 1991) have shown that protection can be achieved at various levels in the susceptible BALB/c mice. Similarly, for example dp72 and GP46/M2 have been used against *Leishmania donovani* and *Leishmania amazonensis* respectively, but only partical protection has been observed (Rachamim and Jaffe, 1993; McMahon-Pratt et al, 1993).

SUMMARY OF THE INVENTION

In these trials, only promastigote derived antigens were used. In the research that led to the present invention it was conceived that vaccines comprising antigens present in different stages of the life cycle of the parasite might increase the percentage of protection. Furthermore, it was found that some proteins are exported as peptides to the macrophage surface and are involved in T-cell mediated immune response towards intracellular parasites. Such parasite antigen(s) involved in inducing protective immunity have not previously been identified. The identification and characterization of such gene products are imperative to allow an understanding of intracellular parasitism as well as the design of diagnostic tests and vaccines.

It is therefore the object of the present invention to provide genes and their derivatives like mRNA or proteins, that may prove to be useful in diagnosis, prophylaxis and treatment of infection by intracellular infectious agents like parasites, in particular trypanosomatids, like Leishmania species.

In the research that led to the invention it was surprisingly found that intracellular proteins of the trypanosomatids in general and Leishmania in particular are capable of inducing immunity against the corresponding parasite species. This was in particular found for histones of these parasites.

The invention pertains to the general finding that intracellular antigens (eg. histones) that are already involved in the T-cell mediated immune response towards intracellular parasites are a good starting point for the design and development of vaccines, pharmaceuticals and diagnostic tests. In the following this principle will be illustrated by reference to trypanosomatids in general and Leishmania species in particular.

The invention in its most basic form thus provides for trypanosomatid histones in substantially isolated form for use as a protective antigen against trypanosomatid infection. The histones may be isolated from the corresponding parasite species but are preferably produced by means of recombinant DNA techniques.

For the latter approach the invention also provides genes encoding the protective histones. Common to these genes is their ability to hybridise to:

a) at least a distinguishing part of the polynucleotide of the sequence depicted in FIG. 6A (SEQ ID NOS:4–5); or b) those parts of the sequence of FIG. 6A (SEQ ID NOS:4–5) that encode a part/parts of the histone that is/are responsible for the protective capacity of the polypeptide; or c) the complemetary strand of either a) or b).

From the above it follows that in its most basic form the recombinant histone may be the complete histone encoded by the gene isolated from the parasite species. In a more advanced embodiment only parts of the gene, either one or more, encoding one or more parts of the histone, at least some of which parts are responsible for its protective capacity, may be used.

The phrase "at least a distinguishing part of the polynucleotide" is intended to indicate that genes of the invention need not necessarily hybridise to the complete sequence depicted in FIG. 6A (SEQ ID NOS:4–5). The invention in fact provides for a gene family the members of which share a sequence similarity and the fact that they encode a histone, in particular histone H1. These two features will enable the skilled person to define the extent to which the sequence of FIG. 6A (SEQ ID NOS:4–5) should hybridise to the other members of the family.

One possibility to establish whether a gene that has been isolated belongs to the family of the invention is comparison of its derived amino acid sequence with an amino acid database, such as the Swiss Prot database or the EMBL database. Such a database will give information on the homology of the derived amino acid sequence with known sequences. On the basis hereof the skilled person can establish whether he actually isolated a histone. A further tool in establishing whether a histone gene was isolated, is chemical and physical characterisation of the gene product. For example, histones are nuclear proteins and bind DNA.

The nucleotide sequence depicted in FIG. 6A (SEQ ID NOS:4–5) is the sequence designated SW3 and already described previously. The invention is intended to encompass both the use of this gene and its derivatives and its family members as defined above.

Furthermore, the invention relates to derivatives of the genes, which derivatives comprise fragments of the gene, complete or partial cDNAs of the gene, complete or partial mRNAs to the gene, complete or partial proteins encoded by the gene, peptides comprising at least an immunogenic part of the protein, antisense oligo- or polynucleotides, fusion products between at least part of the gene, CDNA, mRNA, protein or peptide and at least part of another gene, CDNA, mRNA, protein or peptide, antibodies against the gene, CDNA, mRNA, protein, peptides or fusion products thereof, primers specific for the gene, cDNA or mRNA, wherein each derivative may either be isolated or may be obtained through recombinant DNA techniques. This list is not to be construed as limiting to the invention. For the skilled person the above will be a guide to define derivatives falling within the scope of the invention. These derivatives may be obtained by using commonly known and rather straightforward molecular biological techniques, described for example by Sambrook et al., 1989 (infra).

In this application "gene", "cDNA", "mRNA", "oligonucleotide" and "polynucleotide" as well as their antisense or complementary counterparts may be referred to as "nucleic acids".

"Proteins", "peptides" or "polypeptides" refer to the products obtainable by transcription and translation of the nucleic acids and are generally referred to as "gene products".

These derivatives can be identified by molecular hybridisation to the gene (for antisense polynucleotides or RNAs), by their activity, by their function, by recognizing the gene product or parts thereof (for antibodies), by the immune system as helper or cytotoxic T lymphocyte epitopes.

The invention further relates to expression vectors harboring the nucleic acids for producing mRNA or gene products. Again the skilled person will be very well capable of selecting a suitable vector and the necessary expression signals, such as transcription and translation initiation and termination sequences based on his common knowledge and the information contained in this application.

According to a further aspect thereof the invention provides for probes directed against the nucleic acids, antibodies directed against the gene products, nucleic acid molecules or polypeptides recognising the amino acid sequence of the gene products. The gene product is a nuclear protein that may be isolated due to the fact that it binds to DNA.

Furthermore, the invention provides for diagnostic agents comprising said nucleic acids, antibodies or said gene products for use in assaying infection and thus diagnosing Leishmania infections, and the use of said nucleic acids, antibodies or said gene products for prophylactic purpose, e.g. as component in a vaccine, or in therapy.

In particular this invention relates to intracellular protein, in particular to nucleic acid binding protein, more in particular to nuclear proteins. In particular, this invention relates to histones, and more in particular to histones H1, in particular to histone H1 gene family, isolated by molecular hybridisation or polymerase chain reaction, more in particular to the polypeptide of the SW3 gene.

The gene products, in particular products of the SW3 gene of *Leishmania major* or SW3 analogs of other Leishmania species, were found to elicit a strong immune response and demonstrate protective capacities.

In this invention, an immune response in mice was elicited by injecting a recombinant protein derived from the gene. A specific protection was obtained when the protein was injected sub-cutaneously and animals were subsequently challenged with live parasites. Another example teaches a nuclear polypeptide sequence, histone H1, and its use in immunisation regimens. Cross-hybridising mRNAs were detected in other Leishmania species. More particular the SW3 polypeptide was expressed in *E.coli* as a recombinant protein by a fusion with glutathion S transferase (GST). Mice were immunised with purified GST-SW3 polypeptide. The raised antibodies recognised the injected product. Immunised mice were infected with *Leishmania major*. Specific recognition was observed and protective effect of the polypeptide was shown in challenge experiments.

The present invention is described in the above under reference to *L.major*. However, the invention is also intended to encompass further Leishmania species, such as species of the subgenus Leishmania, comprising the complex *L.major*, which only comprises *L.major* species, the complex *L.donovani*, comprising for example *L.chagasi, L donovani,* and *L.infantum,* and the complex *L.mexicana,* comprising inter alia *L.amazonensis* and *L.mexicana,* as well as species of the subgenus Viannia, comprising the complex *L.braziliensis,* comprising *L.braziliensis* en *L.peruviana* and the complex *L.guyanensis,* comprising the species *L.gyanensis* and *L.panamensis.*

DETAILED DESCRIPTION OF THE INVENTION

The invention is illustrated by the following example which should not be considered as limiting to the scope thereof.

EXAMPLE

1. Materials and Methods

In the following example many techniques that are well known and accessible to those skilled in the art of molecular biology, protein chemistry, immunology and Leishmania biology are utilized. Such methods are not always described in detail. Enzymes are obtained from commercial sources and used according to the suppliers protocols. Bacterial media and current cloning techniques are described in Sambrook et al. (Molecular cloning: a laboratory manual, CSH press 1989).

1.1. Culture of parasites promastigotes and isolation of amastigotes

*Leishmania major* promastigotes (strain LV39-MHRO/ SU/59/P or MRHO/IR/75/ER) are cultivated at 26° C. in Dulbecco's modified Eagle medium (DMEM; Gibco-BRL) on a solid rabbit blood agar (Louis et al, 1979), supplemented with 10% fetal calf serum (Seromed) and gentamicin (10 gg/ml). Amastigotes were produced in vivo. BALB/c mice were injected subcutaneously in the hind footpad with 2 to 5×10$^7$ parasites/ml of stationary phase promastigotes.

Alternatively, amastigotes were obtained by passing parasites in the back of Swiss nude mice. *L.major* amastigotes were purified from back lesions and extracted according to a described protocol (Glaser et al, 1990) .

1.2. Nuclei isolation

Promastigotes are transferred to a 50 ml Falcon tube and centrifuged 5 min at 270×g at 4° C. The pellet is resuspended in 10 ml of cold 1×PBS and transferred to a cold 15 ml Greiner tube and centrifuged as before. The pellet is resuspended in 2 ml of lysis buffer (140 mM NaCl, 1.5 mM MgCl$_2$, 10 mM Tris-HCl (pH 8.6), 0.5% NP-40) containing 40 μl of 200 mM vanadyl ribonucleoside complex (Berger and Birbenmeier, 1979) and vortexed during 10 seconds. Following a centrifugation during 3 min at 6000×g at 4° C., the pellet corresponding to the nuclear fraction and 2 ml of supernatant which can be further processed to extract cytoplasmic RNA, were obtained. The nuclear pellet is frozen in liquid nitrogen and stored at −70° C. Isolation of amastigotes nuclei was performed using a similar protocol.

1.3. Total histones and histone H1 extraction

Histones are soluble in HCl and, among histones, H1 is selectively soluble in perchloric acid. Cells were collected, washed twice in 1×PBS and lysed in 140 mM NaCl, 1.5 mM MgCl$_2$ 10 mM Tris-HCl (pH 8.6), 0.5% NP40. Nuclei were pelleted at 6000 g for 3 min (Kontron). Nuclei were resuspended in 1.25N HCl for total histone extraction or 5% perchloric acid for histone H1 recovery, vortexed for 30 seconds and mixed on a rotating wheel at room temperature for an hour. Insoluble proteins are pelleted at 7000 rpm for 5 min. HCl histone extracts were precipitated with 8 volumes ice cold acetone and H1 perchloric extracts with 8 volumes of cold ethanol. Samples were then centrifuged at 10.000 rpm for 15 min and the pellets were resuspended in sample buffer for analysis by SDS-polyacrylamide gel electrophoresis (SDS-PAGE) and the SW3 nature was confirmed by immunoblotting using α415 petide serum as the detecting antibody. α415 peptide serum is serum produced by immunisation of a rabbit with the 415 peptide described under 1.4.

1.4. Production and purification of antibody

A peptide sequence:

(NH$_2$-MSSNSAAAAVSAATTSPQKS-COOH) (415 peptide, SEQ ID NO:1) deduced from the SW3 cDNA and corresponding to the first twenty amino acids was synthesised. Peptide synthesis was performed according to the F-moc, t-butyl strategy for solid phase synthesis, as described by Merrifield (1986) and Atherion et al. (1988). The peptide was purified by gel filtration by using a SEPHADEX-G25 and its molecular weight was confirmed by mass spectrometry on an LDI 1700 Mass Monitor (Linear Scientific Inc, Reno, Nev.) and shown to be >90% pure. The lyophilized peptide was dissolved in 1×PBS at 2mg/ml and injected into rabbits to raise specific antibodies (performed by Eurogentec SA, Belgium). The obtained serum was called "α415 peptide serum".

1.5. Parasite protein analysis and immunoblotting

Promastigotes were collected by centrifugation (10 min at 3000 revs/min at 4° C.), washed three times in 1×PBS and resuspended in gel sample buffer for SDS-PAGE (Lämmli, 1970). Amastigotes were isolated according to a published method (Glaser et al, 1990) and are then handled as described for promastigotes. Protein gel electrophoresis was performed as described. Routinely, the proteins from 3×10$^7$ cells boiled in 1×Lämmli buffer for 5 min, and loaded in a 4 mm wide slot were separated by 15% SDS-PAGE. Proteins were electrotransferred onto nitro-cellulose (Immunoblots). Immunoblotting from SDS-polyacrylamide gels was carried out as described by Harlow and Lane (1988)

and a 1:1000 dilution of the rabbit α415 peptide serum was added to the filter incubated overnight at room temperature. Goat anti-rabbit secondary antibody and peroxydase conjugated protein A were used and a chemiluminescence reaction substrate (Amersham) was used to reveal presence of reactive polypeptide(s).

1.6. Isolation of the SW3 gene and SW3 homologues cDNA of total *L.major* mRNA or genomic DNA isolated from LV39 strain was used as template in polymerase chain reaction in presence of the oligonucleotides:

S-SW3 (5'-cccgtcgacggatgtcctctaattc-3') (SEQ ID NO:2)
and:
A-SW3 (5'-agagtcgacctatgatgcgtcttcgggcacgt-3') (SEQ ID NO:3)

in a buffer containing 20 mM Tris-HCl (pH 8.3), 100 mM KCl, 3 mM MgCl$_2$, 2.5 mM of each of the dNTPs and one unit of Taq polymerase. Different amplified products cross-hybridising with SW3 were obtained and subcloned in pGemini vectors (Promega Inc.) The nucleotide sequence was determined and deduced amino acid sequences were compared to SW3 amino acid sequence (Fasel et al., 1994).

1.7. RNA isolation and analysis

Cytoplasmic RNA of different Leishmania species was isolated as described previously (Fasel et al., 1994). 15 μg RNA were fractionated on 0.8% agarose gel and transferred to Genescreen plus membrane (NEN research products) Radioactive antisense probes were generated by in vitro transcription of SW3 cDNA inserted in p GEM-½ vectors containing T7 and Sp6 RNA polymerases promotors. Hybridisation and washing were carried out as described (Fasel et al., 1994).

1.8. Sequence comparison

The amino acid sequences were compared to the SWISS PROT sequence data bank and the degree of similarity was assessed by using Multiple Sequence Alignment (http://www2pasteur.fr/-takaia/MAcours/multalign.html).

1.9. Expression of the SW3 in *E.coli*

The open reading frame SW3 was amplified by polymerase chain reaction from the construct pCRII-SW3 (Fasel et al., 1994) using the oligonucleotides:

S-SW3 (5'-cccgtcgacggatgtcctctaattc-3') (SEQ ID NO:2)
and:
A-SW3 (5'-aga gtcgacctatgatgcgtcttcgggcacgt-3") (SEQ ID NO:3)

in a buffer containing 20 mM Tris-HCl (pH 8.3), 100 mM KCl, 3 mM MgCl$_2$, 2.5 mM of each of the dNTPs and one unit of Taq polymerase. The nucleotide sequence in bold characters correspond to SalI restriction sites which can be used to insert the PCR product in the SalI site of an expression vector. Amplification was performed using the following cylces: 8 min at 98° C., 3 min at 60° C., 2 min at 72° C. followed by 33 cycles of one min at 94° C., 1.5 min at 60° C. and 2 min at 72° C. The fragment was inserted into the SalI site of the vector pGEX-KG (Guan and Dixon, 1991) in phase with the reading frame of the glutathion S-transferase (GST). *E.coli* (DH5 α) were transformed by electroporation and the orientation of the insert was determined by HaeIII restriction enxyme which generates a fragment of different length according to the orientation of the insert. Orientation and sequence of the insert was confirmed by double stranded DNA sequencing. The DNA construct named pGEX-KG-415 was further used to obtain expression of a fusion protein GST-SW3. An *E.coli* colony containing the pGEX-KG-415 plasmid was used to inoculate bacterial culture medium (2×TY) supplemented with 100 μg/ml of ampicilline and grown overnight at 37° C. An aliquot was diluted 1:50 in 200 ml of 2×TY containing 100 μg/ml of ampicilline and cultures at 37° C. in 200 ml of 2×TY to an optical density at 600 nm between 0.6 and 0.8 IPTG was added to a final concentration of 1 mM and the culture as incubated for two additional hours.

Purification protocol, adapted from Smith and Johnson, 1988 and Frangioni and Neel, 1993 is performed at 4° C. if not mentioned otherwise Bacteria are collected by centrifugation 15 min 6000×g and washed once with 6 ml of STE (10 mM Tris (pH 8.0), 150 mM NaCl, 1 mM EDTA). Cells are resuspended in 6 ml of STE containing 5 mg/ml of lysozyme. 10 μl of DNase I at a concentration of 10 mg/ml are added to the mix and the solution is incubated 15 min on ice. Dithiothreitol and sarkosyl are added to final concentration of 5 mM and 1.5% respectively. Additional lysis is obtained by two sonication of 30 sec (Sonifier 250, Brandson). The lysate is centrifuged 10 min at 10.000×g and Triton X-100 is added to the supernatant at a final concentration of 1.4% before an incubation of 15 tot 30 min on ice. Fusion protein is then purified by gentle stirring the mix with agarose-glutation beads (Sigma, Nr.G-4510) in 1×PBS for 30 min at room temperature. Beads are sedimented by centrifuging during 5 min at 1000×g and washed 4 to 5 times with 1 ml of cold PBS. Finally fusion protein is eluted from the resin by resuspending the beads in a solution of 10 mM glutathion (pH 8.0)(Merck Nr 4090) and incubating them 10 to 30 min at room temperature with constant stirring. The mix is centrifuged 5 min at 500×g and the supernatant is transferred to a new tube. Elution is repeated 2 to 3 times and the supernatants are pooled. Aliquot of the preparation is analysed by SDS 10% PAGE as described by Lämmli (1970). Fusion protein can be quantified by measuring absorbance at 280 nm or by comparing intensity of the fusion protein after Coomassie R-250 staining with the staining of defined quantities of molecular weight markers.

1.10. Immunisation protocols

Two×25 μl of a 1:1 sonicated mixture of incomplete Freund's adjuvant and, in 1×PBS, 2mg/ml of either GST-415, 415 peptide or GST alone into BALB/c mice subcutaneously. After 4 weeks, a boost was performed with an equivalent material.

1.11. Parasite challenging protocols

Infection was performed by inoculation of 2 to 5×10$^6$ of infectious promastigotes into the right hind footpad, the left footpad serving as internal control. Growth of the lesion was measured every week using a calliper. The sizes of the footpads were plotted against the number of days post-infection.

2. Results

The SW3 gene has a higher expression at the RNA level in the intracellular amastigote stage as compared to the free-living promastigote stage. It encodes a protein with sequence similarity to an histone H1 protein and has been described as an histone H1-like protein (Fasel et al., 1994) but no evidence for it has been provided.

To characterize the SW3 gene product we generated a rabbit antiserum directed against a peptide ("415") corresponding to the amino-terminus of the deduced amino acid sequence of SW3 (see Materials and methods) and analysed cytoplasmic or nuclear lysates of LV39 strain. In immunoblots of *Leishmania major* promastigotes, anti-415 rabbit serum specifically recognized a doublet of proteins of sizes ranging from 17 to 19 kDa in a nuclear extract (FIG. 1, lane d) but not in a cytoplasmic extract (FIG. 1, lane b), demonstrating the nuclear localisation and the existence of at least two related but different nuclear proteins. Detection of two reacting polypeptides is suggestive of presence of two SW3 related genes. No polypeptides of similar size are recognised by rabbit pre-immune serum (FIG. 1, lanes a and c).

Biochemical analysis of the SW3 polypeptide confirmed the histone nature of the encoded polypeptide. SW3 protein can be purified out of a nuclear fraction to a high degree using the histones (HCl) and histone H1 preparative (perchloric acid) method (FIG. 2, lanes b, d and f). No signal is present when the protein extracts are analysed with pre-immune serum (FIG. 2, lanes a, c and e).

Part of the protein was expressed in a bacterial expression system as a fusion protein with glutathion-S-transferase (GST). A product of the expected molecular weight can be detected after purification on a GST-agarose column (FIG. 3, lane c, indicated by arrow 1). Arrow 2 indicates GST-415 fusion protein containing GST linked to 50 amino acids of SW30. The purified recombinant protein mix was injected in susceptible mouse strains (BALB/c) to demonstrate its potential as a protective antigen in parasite challenge experiments. Groups of mice were immunized subcutaneously (at the basis of the tail) either with a mixture of recombinant protein GST-415 and incomplete Freund's adjuvant (FIG. 4, panel D), incomplete Freund's adjuvant alone (FIG. 4, panel A), or a mixture of GST and incomplete Freund's adjuvant (FIG. 4, panel B). The 415 synthetic peptide was also used (FIG. 4, panel C). Mice were infected with $2-5 \times 10^6$ L.major infectious promastigotes in one hind footpad either one month or three months after immunisation. The development of lesions was monitored weekly by measuring the increase of footpad thickness compared to the uninfected contralateral footpad. In the animals injected with the GST-415 recombinant product or with the 415 peptide (FIG. 4, panels D and C, respectively), susceptibility to infection was overcome: although the lesion started to appear as a sign of infection, its growth was arrested and the size of the lesion diminished. Graphs showing the regression of the lesion in the right footpad of mice injected with the peptide 415 or GST-415, is given in FIG. 4. No regression is observed in mice immunised with IFA (panel A) or GST alone (panel B).

Amplification of *Leishmania major* of genomic DNA using primers S-SW3 and A-SW3 to the most 5' and 3' ends of the SW3 coding region has given rise to various PCR products (FIG. 5, lane a). Certain of these products have been subcloned and sequenced. Our sequencing data has confirmed that the sequenced cDNAs differ from SW3 within the open reading frame (deletion of blocks of amino acids). The sequence of two additional members (A3, P3) of the SW3 family is given in FIG. 6 (SEQ ID NOS: 4–9).

Such SW3 and SW3 related polypeptides are interesting if it can be used to control other Leishmania species. For this reason, search for cross-hybridising mRNA transcripts of various sizes have been detected in New World Leishmania species such as *L.chagasi, L.guyanensis, L.panamensis* and *L.amazonensis* (FIG. 7). This result provides evidence for presence of related genes and gene products in other Leishmania which could be used to obtain protection.

Figure 1:
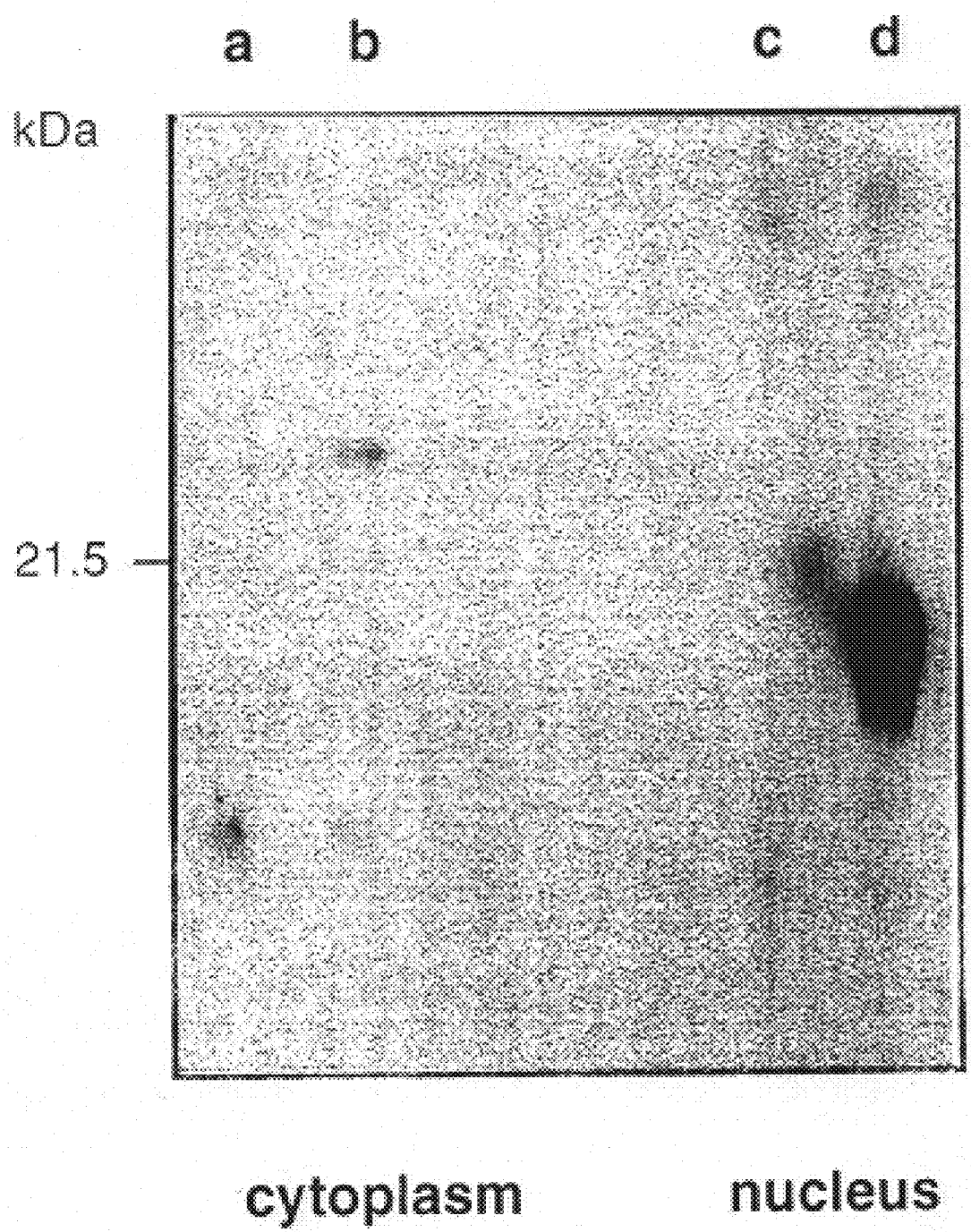
FIG. 1
Figure 2:
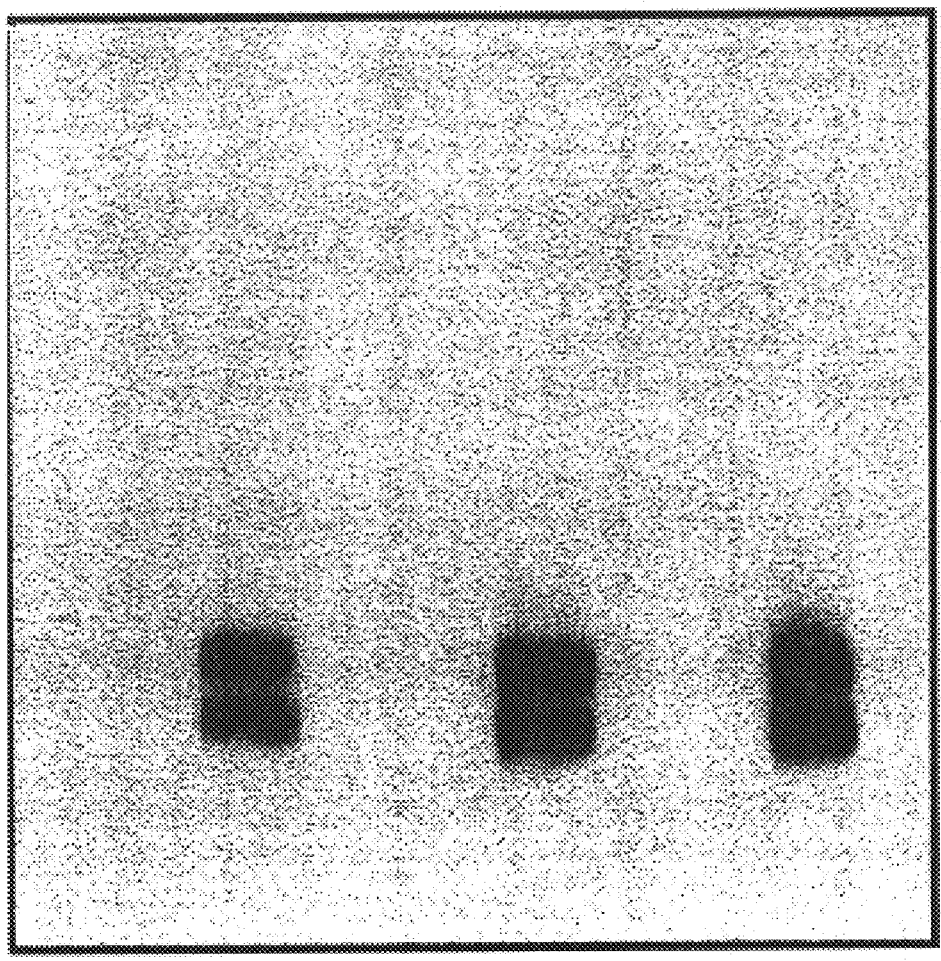
Figure 3:
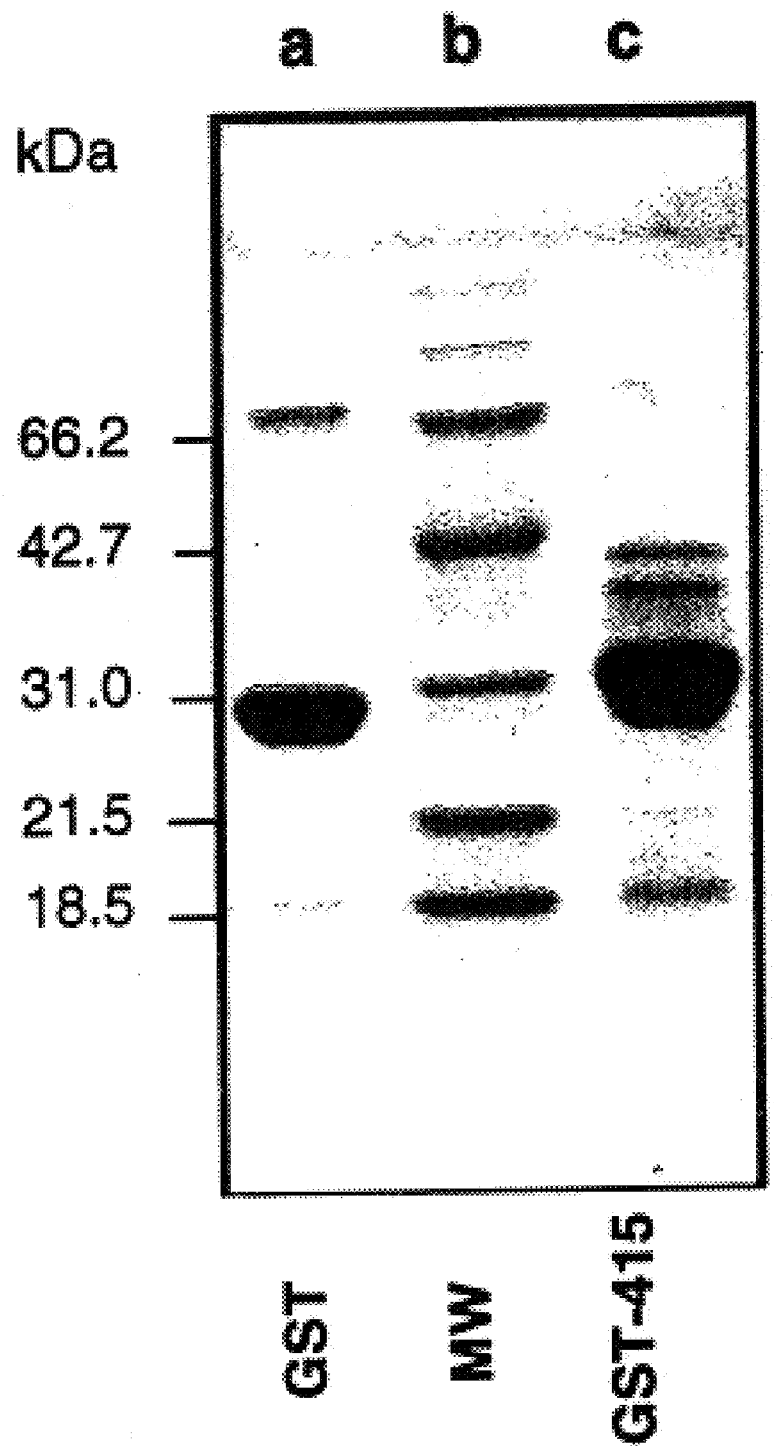
Figure 4A:
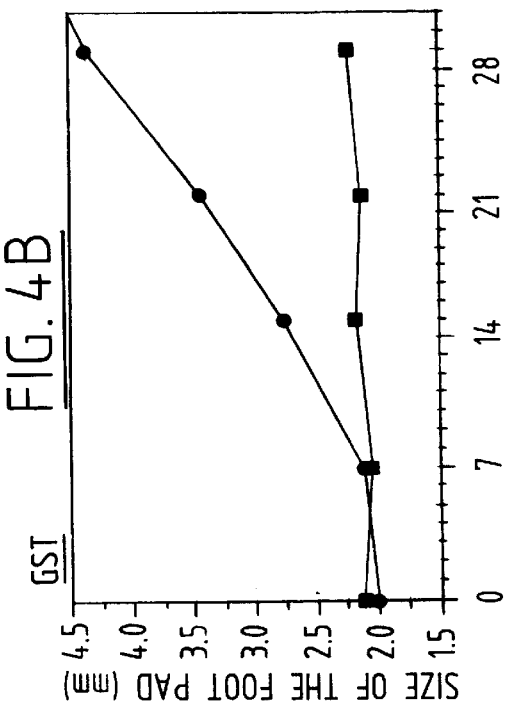
Figure 4B:
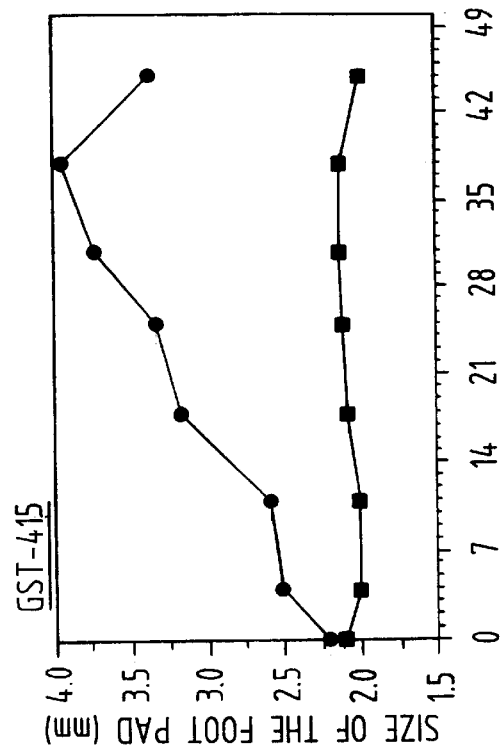
Figure 4C:
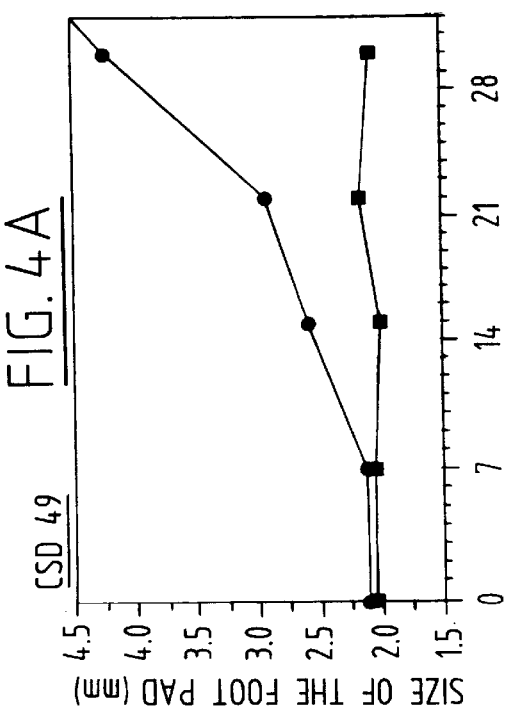
Figure 4D:
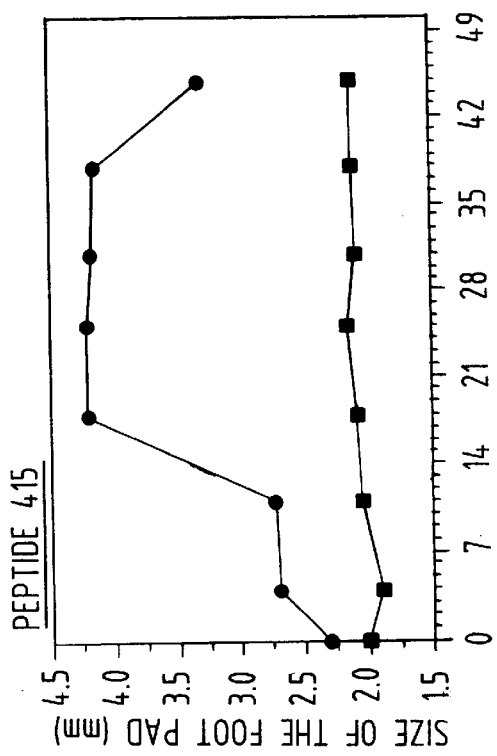

Biochemical localisation of histone H1 by immunoblotting using a rabbit antiserum raised against the peptide 415 corresponding to the N-terminus of the SW3 gene product. Cytoplasmic (lanes a and b) or nuclear (lanes c and d) proteins of stationary phase *Leishmania major* promastigotes were separated on 12.5% SDS-polyacrylamide gels before immunoblotting and probing with rabbit antiserum α-415 (lanes b and d) or with rabbit preimmune serum (lanes a and c). A reference molecular weight (21 kDa) is indicated.

FIG. 2

Biochemical characterisation of the SW3 gene product. Western blot analysis of nuclei (lanes a and b) and of 0.1N HCl (lanes c and d) or 5% perchloric acid (lanes e and f) nuclear extract of stationary phase promastigotes with rabbit antiserum raised against peptide 415 (lanes b, d, and f) or with rabbit preimmune serum (lanes a, c, and f). Extracts were separated on 12.5% SDS-polyacrylamide gels before immunoblotting.

FIG. 3

Expression and purification of the fusion protein GST-415 in *Escherichia coli*. Proteins were separated on a 12.5% SDS polyacrylamide gel and stained with Coomassie blue. The samples were loaded as follows. lane a, purified glutathion-S transferase (GST); lane b, molecular weight markers (MW); lane c, purified fusion protein GST-415 (the full length product is indicated by arrow 1; arrow 2 indicates GST-415 fusion protein containing GST linked to amino acids of SW3 as a result of an internal proteolytic cleavage).

FIGS. 4A–4D

Measurement of the size of the foot pads following infection with *Leishmania major* LV39 strain. BALB/c mice, immunised either IFA (Panel A), with GST (Panel B), with the 415 peptide (Panel C) or the GST-415 fusion protein (Panel D) were infected in the right hind foot pad (filled lozenge symbols) with LV39 parasites. The left foot pad (open lozenge symbols) is used as an internal control.

FIG. 5

Polymerase chain reaction on LV39 genomic DNA using S-SW3 and A-SW3 oligonucleotides (cf. Material and Methods). The samples were loaded as follows: lane a, amplification of LV39 genomic DNA using S-SW3 and A-SW3 oligonucleotides; lane b, negative control corresponding to an amplification in the presence of S-SW3 and A-SW3 but in absence of DNA template; lane c, positive control corresponding to an amplification of SW3 cDNA in the presence of S-SW3 and A-SW3.

FIGS. 6A, 6B and 6C

Comparison of nucleotide and amino acid sequences of SW3 and of two new alleles A3 and P3. Sequences are aligned to obtain maximum similarity using Multiple Sequence Alignment program. FIG. 6A is SEQ ID NO:4, FIG. 6B is SEQ ID NO:6 and FIG. 6C is SEQ ID NO:8

FIGS. 7A–7B

Northern blot analysis of SW3 cross-hybridising mRNAs in other Leishmania species. Panel A: schematic representation of the SW3 transcript, the SW3 gene and of the antisense SW3 riboprobe. Panel B: Cytoplasmic RNA isolated from promastigotes of *L.major* (lane a), *L-guyanensis* (lane b), *L.panamensis* (lane c), *L.chagasi* (lane d) and *L.amazonensis* (lane e) were separated on a 0.8% agarose gel, transferred to a nylon membrane and hybridised with a SW3 anti-sense riboprobe as shown in panel A.

References

Atherton E., Logan C. J. and Shepard R. C. (1988). Peptide synthesis. II. Procedures for solid phase synthesis using Nalpha-fluotenylmetthoxycarbamylamino-acids on polyamide supports: synthesis of substance P and of acyl carrier protein 65–74 decapeptide. J. Chem. Soc. 1, 538

Berger S. L. and Birbenmeier C. S. (1979). Inhibitionof intractable nucleases with ribonucleoside-vandyl complexes: Isolation of messenger ribonucleic acid from resting lymphocytes. Biochemistry 18, 5143

Fasel, N. J., Robyr, D. C., Mauël, J. and Glaser, T. A. (1994). Identification of a histone Hi-like gene expressed in *Leishmania major,* Molec. Biochem. Parasitol. 62, 321.

Frangioni J. V. and Neel B. G. (1993) Solubilization and purification of enzymatically active glutathione S-transferase (pGEX) fusion proteins. Anal. Biochem. 210, 179

Glaser T. A., Wells, S. J., Spithill, T. W., Pettit, J. M., Humphris, D. C., and Mukkuda, A. J. (1990) *Leishmania major* and *donovani:* a method for rapid purification of amastigotes Exp. Parasitology 71, 343.

Guan, K. and Dixon, J. E. (1991) Eukaryotic proteins expressed in *Escherichia coli:* an improved thrombin cleavage and purification procedure of fusion proteins with glutathione S- transferase. Anal. Biochem. 192, 262.

Harlow, E. and Lane, D. (1988). Antibodies: A laboratory manual. Cold Spring Harbor Laboratory, Cold Spring Harbor, N.Y.

Hecker, H., Betschart, B., Burri, M, and Schlimme, W. (1995). Functional morphology of Trypanosome chromatin. Parasitology Today 11, 79

Heinzel, F. P., Schoenhaut, D., S., Rerko, R. M., Rosser, L. E. and Gately, M. K. (1993). Recombinant interleukin 12 cures mice infected with *Leishmania major.* J. Exp. Med. 177, 1505.

Heinzel, F. P., Sadick, M. D., Mutha, S. S. and Locksley, R. M. (1991). Production of interferon-g, interleukin 2, interleukin 4, and interleukin 10 by CD4[+] lymphocytes in vivo during healing and progressive leishmaniasis. Proc. Natl. Acad. Sci. USA. 88, 7011.

Hill, J. O., Awwad, M. and North, R. J. (1989). Elimination of CD4[+] suppressor T cells from susceptible BALB/c mice releases CD8[+] lymphocytes to mediate protective immunity against Leishmania. J. Exp. Med. 169, 1819.

Laemmli, U. (1970) Cleavage of structural proteins during the assembly of the head of the bacteriophage T4. Nature 227, 680.

Louis, J., Moedder, E., Behin, R. and Engers, H. (1979) Recognition of protozoan parasite antigens by murine T lymphocytes. I. Induction of specific T lymphocyte-dependent proliferative response to Leishmania tropica. Europeaan Journal of Immunology 9, 841.

Liew, F. Y. and O'Donnell, C. A. (1993). Immunology of leishmaniasis. Adv. Parasitol. 32, 161.

McMahon-Pratt D., Rodriguez, D., Rodiguez, JR., Zhang Y., Manson K., Bergman, C., Rivas, L., Rodrigue JF., Lohman KL., Ruddle NH. et al., (1993). Recombinant vaccinia viruses expressing GP46/M-2 protect against Leishmania infection. Infection and Immunity. 61, 3351.

Merrifield, R. B. (1986) Solid phase synthesis. Science 232, 341.

Milon, G., Del Giudice, G., and Louis, J. (1995). Immunobiology of experimental cutaneous leishmaniasis. Parasitology Today. 11, 244.

Müller, I., Pedrazzini, T., Farrell, J. P. and Louis, J. (1989). T-cell responses and immunity to experimental infection with *Leishmania major.* Ann. Rev. Immunol. 7, 561.

Rachamim, N. and Jaffe, CL. (1993). Pure protein from *Leishmania donovani* protects mice against both cutaneous and visceral leishmaniasis. Journal of Immunology. 150, 2322.

Reiner, S. L., and Locksley, R. M. (1995). The regulation of immunity to *Leishnmania major.* Annu. Rev. Immunol. 13, 151

Reed, S. G., and Scott, P. (1993). T-cell cytokine reponses in leishmaniasis. Current Opin. Immunol. 5, 524.

Russell, D. G. and Alexander, J. (1988). Effective immunization against cutaneous leishmaniasis with defined membrane antigens reconstituted in liposomes. J. Immunol. 140, 1274.

Scott,P., Pearce,P., Natovitz, and Sher, A. (1988). Vaccination against cutaneous leishmaniasis in amurine model. I. Induction of protective immunity with a soluble extract of promastigotes. J. Immunol. 139, 221.

Scott, P. (1989). The role of Th1 and Th2 cells in experimental cutaneous leishmaniasis. Exp. Parasitol. 68, 369.

Smith, D. F., Gokool, S., Keen, J. K., McKean, P. G. and Rangarajan, D. (1994). Structure and function of infective stage proteins of Leishmania. Biochem. Soc. Trans. 22, 286.

Smith, D. B. and Johnson, K. S. (1988) Single-step purification of polypeptides expressed in *Escherichia coli* as fusions with glutathione S-transferase. Gene 67, 31

Sypek, J. P., Chung, C. L., Mayor, S. E. H., Subramanyam, J. M., Goldmann, S. J., Sieburth, D. S., Wolf, S. F. and Shaub, R. G. (1993). Resolution of cutaneous leishmaniasis: interleukin 12 initiates a protective T helper type 1 immune response. J. Exp. Med. 177, 1797.

Wilson, M. E. (1990). Leishmaniasis. Current Opin. Infect. Dis. 3, 420.

Yang, D. M., Rogers, M. V., and Liew, F. Y. (1991). Identification and characterization of host protective epitopes of a major surface glycoprotein (gp639 from *Leishmania major.* Immunology. 145, 2281.

What is claimed is:

1. Leishania gone encoding a histone polypeptide, said polypeptide having protective capacity against leishmaniasis, and said gene having a nucleotide sequence that specifically hybridizes with:
   a) those portions of the sequence depicted in FIG. 6A (SEQ ID NO:4) that are protective with respect to a Leishmania organism;
   b) those portions of the sequence of FIG. 6A (SEQ ID NO:4) that encode a part/parts of the histone that is/are protective with respect to a Leishmania organism; or
   c) a complementary strand of (either a) or b).

2. Leishmania gene as claimed in claim 1, which is obtained from L. major and has a coding region comprising the nucleotide sequence depicted in FIG. 6B (SEQ ID NO:6), or the complementary strand thereof.

3. Leishmania gene as claimed in claim 1, which is obtained from L. major and has a coding region comprising the mucleotide sequence depicted in FIG. 6C (SEQ ID NO:8), or the complementary strand thereof.

4. A method of therapy for a Leishmania infection comprising administering a gene according to claim 1 to an individual in need of such therapy.

5. The method of claim 4 wherein the Leishmania infection is caused by at least one organism selected from the group consisting of L. major, L. chagasi, L. donovani, L. infantum, L. mexicana, L. amazonensis, L. braziliensis, L. peruviana, L. guyanenesis and L. panamensis.

6. Leishmania gene according to claim 1 encoding an H1 histone.

7. A method of diagnosis of a Leishmania infection comprising combining a gene according to claim 1 with a biological sample from an individual, detecting the presence or absence of a reaction between said gene with said sample, the presence of a reaction being indicative of the presence of said infection.

8. The method of claim 7 wherein the Leishmania infection is caused by at least one organism selected from the group consisting of

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 20 amino acids
      (B) TYPE: amino acid
      (D) TOPOLOGY: linear (xi) SEQUENCE DESCRIPTION: SEQ ID NO:1:

```
Met Ser Ser Asn Ser Ala Ala Ala Val Ser Ala Ala Thr Thr
 1               5                  10                 15

Ser Pro Gln Lys Ser
                 20

(2) INFORMATION FOR SEQ ID NO:2:

(i) SEQUENCE CHARACTERISTICS:
        (A) LENGTH: 25 nucleotides
        (B) TYPE: nucleotide
        (C) STRANDEDNESS: single
        (D) TOPOLOGY: linear (xi) SEQUENCE DESCRIPTION: SEQ ID NO:2:

CCCGTCGACG GATGTCCTCT AATTC                                       25

(2) INFORMATION FOR SEQ ID NO:3:

(i) SEQUENCE CHARACTERISTICS:
        (A) LENGTH: 32 nucleotides
        (B) TYPE: nucleotide
        (C) STRANDEDNESS: single
        (D) TOPOLOGY: linear (xi) SEQUENCE DESCRIPTION: SEQ ID NO:3:

AGAGTCGACC TATGATGCGT CTTCGGGCAC GT                               32

(2) INFORMATION FOR SEQ ID NO:4:

(i) SEQUENCE CHARACTERISTICS:
        (A) LENGTH: 360 nucleotides
        (B) TYPE: nucleotide
        (C) STRANDEDNESS: single
        (D) TOPOLOGY: linear (xi) SEQUENCE DESCRIPTION: SEQ ID NO:4:

ATGTCCTCTA ATTCCGCCGC TGCTGCCGTT TCCGCCGCCA CGACCTCGCC            50

GCAGAAGTCT TCTCGCTCGT CGCCGAAGAG GGCGGCCGTG GGCAAGAAGA           100

CCGGCGCGAA GAAGGTTGCC AAGAAGACCG GCGCGAAGAA GGTTGCGAAG           150

AAGCCAGCGA AGAAGGTTGT GAAGAAGCCA GCGAAGAAGG TTGTGAAGAA           200

GCCAGCGAAG AAGGTTGTGA AGAAGGCTGT GAAGGCTGTG AAGAAGGCTG           250

TGAAGAAGGT TGTGAAGGCT GTGAAGACCG CGAAGAAGTC GTCGAAGAAA           300

TCCTCGGCGA AGAAGTAAGG TGCGCCATCA TGCTTGCCCG TGGCTGACTG           350

TACGCTCTTC                                                       360

(2) INFORMATION FOR SEQ ID NO:5:

(i) SEQUENCE CHARACTERISTICS:
        (A) LENGTH: 105 amino acids
        (B) TYPE: amino acid
        (D) TOPOLOGY: linear (xi) SEQUENCE DESCRIPTION: SEQ ID NO:5:

Met Ser Ser Asn Ser Ala Ala Ala Val Ser Ala Ala Thr Thr
 1               5                  10                 15

Ser Pro Gln Lys Ser Ser Arg Ser Ser Pro Lys Arg Ala Ala Val
                 20              25                  30

Gly Lys Lys Thr Gly Ala Lys Lys Val Ala Lys Thr Gly Ala
                 35              40                  45

Lys Lys Val Ala Lys Lys Pro Ala Lys Val Val Lys Lys Pro
                 50              55                  60
```

```
Ala Lys Lys Val Val Lys Pro Ala Lys Val Val Lys Lys
                65              70              75

Ala Val Lys Ala Val Lys Lys Ala Val Lys Val Val Lys Ala
            80              85              90

Val Lys Thr Ala Lys Lys Ser Ser Lys Lys Ser Ser Ala Lys Lys
        95              100             105
```

(2) INFORMATION FOR SEQ ID NO:6:

(i) SEQUENCE CHARACTERISTICS:
        (A) LENGTH: 300 nucleotides
        (B) TYPE: nucleotide
        (C) STRANDEDNESS: single
        (D) TOPOLOGY: linear (xi) SEQUENCE DESCRIPTION: SEQ ID NO:6:

```
ATGTCCTCTA ATTCCGCCGC TGCTGCCGTT TCCGCCGCCA CGACCTCGCC          50

GCAGAAGTCT TCTCGCTCGT CGCCGAAGAG GGCGGCCGTG GCCAAGAAGA         100

CCGGCGCGAA GAAGGTTGCG AAGAAGCCAG CGAAGAAGGT TGCGGAGAAG         150

CCAGCGAAGA AGGTTGTGAA GAAGCCAGCG AAGAAGGTTG TGAAGAAGGC         200

TGTGAAGGCT GTGAAGAAGG CTGTGAAGAA GGTTGTGAAG GCTGTGAAGA         250

CCGCGAAGAA GTCGTCGAAT AAATCCTCGG CGAAGAAGTA AGGTGCGCCA         300
```

(2) INFORMATION FOR SEQ ID NO:7:

(i) SEQUENCE CHARACTERISTICS:
        (A) LENGTH: 96 amino acids
        (B) TYPE: amino acid
        (D) TOPOLOGY: linear (xi) SEQUENCE DESCRIPTION: SEQ ID NO:7:

```
Met Ser Ser Asn Ser Ala Ala Ala Ala Val Ser Ala Ala Thr Thr
 1               5                   10                  15

Ser Pro Gln Lys Ser Ser Arg Ser Ser Pro Lys Arg Ala Ala Val
                20                  25                  30

Ala Lys Lys Thr Gly Ala Lys Lys Val Ala Lys Lys Pro Ala Lys
                35                  40                  45

Lys Val Ala Glu Lys Pro Ala Lys Val Val Lys Lys Pro Ala
                50                  55                  60

Lys Lys Val Val Lys Ala Val Lys Ala Val Lys Lys Ala Val
                65                  70                  75

Lys Lys Val Val Lys Ala Val Lys Thr Ala Lys Lys Ser Ser Asn
                80                  85                  90

Lys Ser Ser Ala Lys Lys
                95
```

(2) INFORMATION FOR SEQ ID NO:8:

(i) SEQUENCE CHARACTERISTICS:
        (A) LENGTH: 300 nucleotides
        (B) TYPE: nucleotide
        (C) STRANDEDNESS: single
        (D) TOPOLOGY: linear (xi) SEQUENCE DESCRIPTION: SEQ ID NO:8:

```
ATGTCCTCTA ATTCCGCCGC TGCTGCCGTT TCCGCCGCCA CGACCTCGCC          50

GCAGAAGTCT TCTCGCTCGT CGCCGAAGAG GGCGGCCGTG GGCAAGAAGA         100

CCGGCGCGAA GAAGGTTGCC AAGAAGCCAG CGAAGAAGGT TGCGGAGAAG         150
```

```
CCAGCGAAGA AGGTTGTGAA GAAGCCAGCG AAGAAGGTTG TGAAGAAGGC        200

TGTGAAGGCT GTGAAGAAGG CTGTGAAGAA GGTTGTGAAG GCTGTGAAGA        250

CCGCGAAGAA GTCGTCGAAG AAATCCTCGG CGAAGAAGTA AGGTGCGCCA        300

(2) INFORMATION FOR SEQ ID NO:9:

(i) SEQUENCE CHARACTERISTICS:
        (A) LENGTH: 96 amino acids
        (B) TYPE: amino acid
        (D) TOPOLOGY: linear (xi) SEQUENCE DESCRIPTION: SEQ ID NO:9:

Met Ser Ser Asn Ser Ala Ala Ala Val Ser Ala Ala Thr Thr
1               5                   10                  15

Ser Pro Gln Lys Ser Ser Arg Ser Ser Pro Lys Arg Ala Ala Val
                20                  25                  30

Gly Lys Lys Thr Gly Ala Lys Lys Val Ala Lys Lys Pro Ala Lys
                35                  40                  45

Lys Val Ala Glu Lys Pro Ala Lys Lys Val Val Ala Lys Pro Ala
                50                  55                  60

Lys Lys Val Val Lys Lys Ala Val Lys Ala Val Lys Lys Ala Val
                65                  70                  75

Lys Lys Val Val Lys Ala Val Lys Thr Ala Lys Lys Ser Ser Lys
                80                  85                  90

Lys Ser Ser Ala Lys Lys
                95
```